US005578652A

United States Patent [19]
Blanpied et al.

[11] Patent Number: 5,578,652
[45] Date of Patent: Nov. 26, 1996

[54] METHOD OF PRODUCING RIGID FOAMS AND PRODUCTS PRODUCED THEREFROM

[75] Inventors: Robert H. Blanpied; James D. Thornsberry, both of Meridian, Miss.

[73] Assignee: Exxon Chemical Patents, Inc., Wilmington, Del.

[21] Appl. No.: 498,276

[22] Filed: Jul. 3, 1995

Related U.S. Application Data

[63] Continuation-in-part of Ser. No. 389,955, Feb. 17, 1995, abandoned.

[51] Int. Cl.$^6$ .................................................. C08J 9/14
[52] U.S. Cl. .......................... 521/107; 521/125; 521/130; 521/131; 521/172
[58] Field of Search ..................................... 521/107, 125, 521/130, 131, 172

[56] References Cited

U.S. PATENT DOCUMENTS

| | | |
|---|---|---|
| 3,558,531 | 1/1971 | Sayler . |
| 4,178,455 | 12/1979 | Hirai et al. . |
| 4,721,823 | 1/1988 | Venier et al. . |
| 4,929,782 | 5/1990 | Venier et al. . |
| 5,096,933 | 3/1992 | Volkert . |
| 5,166,182 | 11/1992 | Blanpied . |
| 5,182,309 | 1/1993 | Hutzen . |
| 5,336,696 | 8/1994 | Ashida . |

FOREIGN PATENT DOCUMENTS

| | | |
|---|---|---|
| 2595092 | 3/1986 | France . |
| 2595093 | 3/1986 | France . |
| 1115145 | 5/1968 | United Kingdom . |
| 1264255 | 2/1972 | United Kingdom . |
| 1302481 | 1/1973 | United Kingdom . |
| 2271575 | 4/1994 | United Kingdom . |
| 2273107 | 6/1994 | United Kingdom . |

OTHER PUBLICATIONS

Chemical Abstracts 112:219195g, "Catalystic Momerization of Dicyclopentadiene on y—aluminum oxide in a Continuous–Flow System", Gasanov et al.

Chemical Abstracts 113:175183q, "Catalytic Cracking of Naphthenes and Naphtheno–armoatcis in Fixed Bed Micro Reactors", Mostad et al.

"Hydrocarbons Study Report Final Draft", Ozone Operations Resource Group Production Sector (Mar. 17, 1995).

Pauling, Linus, "College Chemistry", Section 26–6, The Plantinum Metals, pp. 544–547 (1951).

Kirk–Othmer Encyclopedia of Chemistry, vol. 7, "Cyclopentadiene and Dicyclopentadiene", pp. 417–429.

Kirk–Othmer Encyclopdia of Chemistry, vol. 12, "Pentanes", pp. 919–925.

Chemical Abstracts 110:39391t, "Thermocatalytic Conversion of Cyclopentadiene", Gasanov et al.

Chemical Abstracts 109:57022g, "Alloy Membrane Catalysts For the Hydrogenation of Unsaturated Hydrocarbons and Procedure For Their Preparation", Gryaznov, et al.

Chemical Abstracts 109:57024j, "Alloys Membrane Catalysts For cyclization of 1,3—pentadiene To Cyclopentane and Cyclopentene", Gryaznov et al.

Chemical Abstracts 116:197581h, "Catalytic Conversion of *Hevea brasiliensis* and *Virola sebifera* Oils To Hydrocarbon Fuels", Da Rocha Filho, et al.

Chemical Abstracts 115:255409a, "Influence of Thermodiffusive and Chemical Treatment of Membrane Catalyst Surfaces Formed From Alloys of Palladium with Rhodium or Ruthenium On Hydrogenation of 1,3—pentadiene", Mishchenko et al.

Chemical Abstracts 114:249713h, "Direct and Indirect Promotion of Palladium/Y by Calcium (2+) Ions", Bai, Zhang, and Sachtler.

*Primary Examiner*—Morton Foelak
*Attorney, Agent, or Firm*—John F. Hunt; Richard D. Jordan

[57] ABSTRACT

A thermosetting plastic foam solid is obtained using a blowing agent comprised at least partially from depolymerization of dicyclopentadiene into essentially pure cyclopentane. This unique hydrocarbon is miscible in polyester polyols, where others, such as extracted cyclopentane, are not. In a blend of 15 parts of liquid flame retardant per hundred parts polyester polyol, the mixture is both stable and has a suitably low viscosity.

15 Claims, No Drawings

METHOD OF PRODUCING RIGID FOAMS AND PRODUCTS PRODUCED THEREFROM

This application is a continuation-in-part application of U.S. patent application Ser. No. 08/389,955, filed Feb. 17, 1995, which is incorporated herein by reference.

BACKGROUND

1. Field of Invention

This invention pertains to methods of producing thermosetting plastic foams utilizing any suitable catalyst to create exothermic heat, which heat in turn causes the unique expansion agent of this invention to vaporize, thereby creating small cells and a low density thermoplastic foam, as well as foams produced by such methods. Examples of such foams include polyurethane foams, polyurethane modified polyisocyanurate foams, and condensation reaction foams such as the formaldehyde series of urea, melamine, and phenol used for thermal insulation.

2. Related Art and Other Considerations

Cellular organic rigid thermosetting plastic foams used for thermal insulation are well known in the art. Such foams can be made with urethane linkages, or made with a combination of both isocyanurate linkages and urethane linkages, or they can be made via the well known condensation reactions of formaldehyde with phenol, urea, and melamine. All such plastic foams must utilize an expansion agent, often referred to as a "blowing agent".

The prior art is replete with references to techniques of expanding foam cells. For many years, the dominant blowing agent for all thermosetting foams was trichloromonofluoromethane (CFC-11). Other types of blowing agents have been proposed, such as the use of hydrocarbon mixtures, taught in U.S. Pat. No. 3,558,531. In recent years, various foam expansion methods have been taught in such United States patents as the following (all of which are incorporated herein by reference):

U.S. Pat. Nos. 3,993,609, 4,636,529, 4,898,893, 4,927,863, 4,981,876, 4,981,880, 4,986,930, 4,996,242, 5,032,623, 5,070,113, 5,096,933, 5,114,986, 5,130,345, 5,166,182 5,182,309, 5,205,956, 5,213,707, 5,227,088, 5,234,967, 5,236,611, 5,248,433, 5,262,077, 5,277,834, 5,278,196, 5,283,003, 5,290,823, 5,296,516, 5,304,320, 5,314,926, 5,318,996, and 5,336,696.

The relatively recent hydrogenated chlorofluorocarbons (called "HCFCs") are considered to be environmentally friendly expansion agents, but still contain some chlorine, and therefore have an "Ozone Depletion Potential" (called "ODP"). Because of the ODP, the HCFCs have been mandated for eventual phaseout.

Another known class of blowing agents is the non-chloronated, partially hydrogenated fluorocarbons (called "HFCs") which have the general formula: $H_xF_yC_z$, where x, y, and z are integers. The HFC compounds being proposed for future blowing agents have two serious defects: (1) high intrinsic thermal conductivity properties (i.e., poor thermal insulation); and, (2) expense. In view of the fact that approximately ten percent by weight of rigid foam insulation are the compounds used as blowing agents, high cost combined with the poor insulating value render HFCs less attractive candidates for blowing agents in commercial foam insulation.

Hydrocarbon blowing agents are also known, which class includes halogen-free and $CO_2$-free blowing agents. For example, U.S. Pat. No. 5,182,309 to Hutzen teaches the use of iso- and normal-pentane in various emulsion mixtures. Another example of hydrocarbon blowing agents is taught by Volkert in U.S. Pat. No. 5,096,933, pointing out the virtues of commercial cyclopentane distilled and extracted from natural gas wells.

However, the hydrocarbon blowing agents mentioned in connection with such prior art have inadequate miscibility with polyester polyols, commonly used in polyisocyanurate modified polyurethane foam. The use of these alkanes require a chemical surfactant to obtain a suitable mixture. An improvement in the problem of poor miscibility is taught in U.S. Pat. No. 5,166,182 to Blanpied, whereby the use of azeotropes with polar organic solvents enhance the miscibility with polar polyester polyols. However, all of that work was done using cyclopentane extracted from natural gas.

Another problem with some of these alkanes is the poor insulating value. For example, the thermal conductivity of n-butane at 25° C. is 16.3 mW/m*°K., and n-pentane at 25° C. is 14.8 mW/m*°K.

None of the prior art patents known to Applicants discuss how the cyclopentane is obtained for the disclosed foaming process, nor is there any recognition that any certain mode of cyclopentane production may endow the cyclopentane with properties which are beneficial for a foaming operation.

Although some cyclopentane originates from petroleum, most cyclopentane originates from natural gas wells, and is extracted as the bottom layer of distillation in a refinery, allowing the lighter molecules to be transferred through the natural gas pipeline network. Cyclopentane obtained by extraction contains impurities. In fact, cyclopentane sold as "Technical Grade" contains from 22% to 30% impurities.

Extracted cyclopentane ("EXTRCP") has at least five problems which heretofore virtually prohibited it from being considered a serious candidate as a commercial blowing agent for rigid foam insulation. The first problem is that its limited supply is considerably below the amount needed to meet the quantity demanded of a commercial compound. The second problem is that this inadequate supply contains at least twenty-two percent impurities in the form of hexane isomers and n-pentane, which impurities significantly reduce insulating value of foam made therefrom. The third problem is that extracted cyclopentane is not miscible with the common polyester polyols which are used with HCFCs, nor those that were used with CFC-11.

The fourth problem is that extracted cyclopentane does not reduce the viscosity of the polyester polyol foamable blend to a workable level, even when liquid fire retardants are utilized.

The fifth problem is that the foam produced with EXTRCP will not pass the ASTM E-84 maximum 75 Flame Spread Index even with moderate flame retardant.

With respect to the third and fourth above-mentioned problems, the above-discussed U.S. Pat. No. 5,096,933 to Volkert, while generally alluding to the use of polyester polyols, provides no specific example using polyester polyols. The lack of any specific example is consistent with the present inventors' understanding that mixtures made from polyester polyols and extracted cyclopentane are unstable mixtures. In this regard, extracted cyclopentane is no more suitable as a miscible blowing agent than n-pentane or iso-pentane. All three require chemical surfactants for miscibility.

Perhaps the largest obstacle to the use of hydrocarbon blowing agents in the United States is the fifth problem—flammability of thermoset plastics blown with hydrocarbon blowing agents. U.S. Pat. No. 5,096,933 to Volkert mentions disadvantages caused by the flammability of the cycloalkanes. Volkert alludes to the optional use of flame retardants, but provides no example utilizing a flame retardant. Furthermore, none of the five Polyurethane Rigid Foam examples shown by Volkert would pass the maximum Flame Spread Index (FSI) of 75 (ASTM E-84) required of construction foam in the United States. Likewise, a polyisocyanurate foam, without flame retardant, having an Isocyanate-to-Polyester Polyol INDEX of 2.3 badly failed the ASTM E-84 maximum Flame Spread Index requirement of 75, by achieving a 2174 FSI.

With regard to flammability, it is well known that organic surfactants contribute to the flammability of rigid plastic foam insulation. The three main classes of organic surfactants (anionic, cationic, and nonionic) all add to the flammability problem of plastic foam. However, the use of organic carbonates, such as ethylene carbonate and propylene carbonate, does not increase the flammability of plastic foam.

TABLE I describes experiments attesting to the immiscibility of extracted cyclopentane with the polyester polyol having the most miscible potential with non-polar hydrocarbons, as well as the immiscibility of n-pentane and iso-pentane with this polyester polyol. The first column of TABLE I shows the weight ratio of polyester polyol to hydrocarbon blowing agent, with the proposed blowing agents n-pentane, iso-pentane, and extracted cyclopentane being shown in the second through fourth columns, respectively. In all experiments, the polyester polyol utilized was Stepanpol PS-2502A, which (along with Cape's 245-C) is known to have the best miscibility with non-polar hydrocarbon blowing agents. In the experiments reflected by the first row of TABLE I, pure (no other chemicals) PS-2502A polyol was used at 80% weight with 20% by weight pentane; and so forth as indicated in the first column of TABLE I. Significantly, all experiments showed the polyester polyol to be immiscible with extracted cyclopentane, just as it is with n-pentane and iso-pentane.

TABLE I

IMMISCIBILITY STUDIES

| Weight Ratio (Polyol/ Blowing Agent) | N-Pentane | Iso-Pentane | Extracted Cyclopentane |
| --- | --- | --- | --- |
| 80/20 | Separates | Separates | Separates |
| 75/25 | Separates | Separates | Separates |
| 70/30 | Separates | Separates | Separates |
| 50/50 | Separates | Separates | Separates |
| 35/65 | Separates | Separates | Separates |
| 20/80 | Separates | Separates | Separates |

The fourth problem of extracted cyclopentane (EXTRCP) is shown in TABLE II below, where viscosity is high when blended in foamable blends;.

TABLE II shows that, without exception, every foamable blend made with extracted cyclopentane produced a Brookfield viscosity over 1000 cps at 65° F., even one with 10 parts by weight of a strong viscosity reducer, Texaco's NP-95. The foamable blends using both Fyrol PCF and Propylene Carbonate mixed into an unstable emulsion which soon separated. The inability to formulate with both liquid flame retardant and an organic carbonate is a serious obstacle to obtaining both flame resistance and a low enough viscosity to be workable.

In addition to obtaining cyclopentane by extraction, it appears that cyclopentane can also be synthesized from other hydrocarbons. In this regard, French Demande FR 2,595,092 and FR 2,595,093 teach the preparation of catalysts comprised of palladium with another transition metal such as ruthenium or rhodium for the cyclization and hydrogenation of 1,3-pentadiene, as well as the hydrogenation of cyclopentadiene, to cyclopentane. These French Demandes do not teach or suggest the synthesis of cyclopentane from dicyclopentadiene ("DCP"), or make any reference to foaming processes.

British Specifications GB 2,271,575A and GB 2,273,107A disclose two similar methods for synthesizing cyclopentane from dicyclopentadiene. Likewise, British Specification GB 1,302,481 teaches a method which synthesizes minor amounts of cyclopentane, but preferentially produces cyclopentene. While British Specifications GB 2,271,575A and GB 2,273,107A mention initially the search for blowing agents for polyurethane foam, neither provides an example of the use of cyclopentane as a blowing agent for foam, much less a foam produced with polyester polyol. In fact, European practice is to make polyurethane foam using polyether polyol rather than polyisocyanurate foam using polyester polyol.

Historically, considerable attention has been directed to the synthesis of cyclopentadiene and various isomers of the pentadiene and pentene building-block monomers. In this regard, dicyclopentadiene ("DCP"), $C_{10}H_{12}$, is the dimer of cyclopentadiene ("CP"), $C_5H_6$, and is the naturally stable form of CP. Cyclopentadiene monomer spontaneously dimerizes at room temperature. DCP is obtained from the thermal cracking of high molecular weight hydrocarbons, such as naphtha and gas oils, particularly in the presence of steam.

Owing to its conjugated double bonds, CP can undergo numerous reactions, and has several important commercial uses. While most commercial CP is obtained from cracking DCP, CP is also obtained from other commercial reactions such as ethylene production. To prevent it from autodimerizing, CP must be cooled to below minus 20 degrees Celsius. To prevent spontaneous oxidation, CP must be protected

TABLE II

| CHEMICALS: | Pbw | Pbw | Pbw | Pbw | Pbw | Pbw | Pbw | Pbw | Pbw | Pbw |
| --- | --- | --- | --- | --- | --- | --- | --- | --- | --- | --- |
| PS-2502A | 100 | 100 | 100 | 100 | 100 | 100 | 100 | 100 | 100 | 100 |
| Fyrol PCF | — | — | — | — | — | 15 | 15 | 15 | 15 | 15 |
| Dabco K-15 | 4.0 | 4.0 | 4.0 | 4.0 | 4.0 | 4.0 | 4.0 | 4.0 | 4.0 | 4.0 |
| PM-DETA | 0.2 | 0.2 | 0.2 | 0.2 | 0.2 | 0.2 | 0.2 | 0.2 | 0.2 | 0.2 |
| DC-5357 | 2.0 | 2.0 | 2.0 | 2.0 | 2.0 | 2.0 | 2.0 | 2.0 | 2.0 | 2.0 |
| Water | — | — | — | — | — | 1.8 | 1.8 | 1.8 | 1.8 | 1.8 |
| Prop Carb | — | 5.0 | 10 | — | — | — | 5.0 | 10 | — | — |
| Tex NP-95 | — | — | — | 5.0 | 10 | — | — | — | 5.0 | 10 |
| EXTRCP | 20. | 20. | 20. | 20. | 20. | 23. | 23. | 23. | 23. | 23. |
| Brookfield Viscosity cps at 65° F. = | 6928 | 4016 | 2392 | 4480 | 2880 | 2725 | Broke* | Broke* | 1810 | 1124 |

* = unstable emulsion separated (broke) rapidly from atmospheric oxygen. Thus, it is advantageous to convert DCP into cyclopentane in an enclosed reactor utilizing an excess of hydrogen, and adding cyclopentane as a diluent, as shown in GB 2,271,575A and GB 2,273,107A.

The thermocatalytic conversion of DCP to CP, and back again, and similar processes, have been well documented. However, such conversion and similar processes have not occurred in the context of utilization for a blowing agent for a rigid insulative foam which utilizes polyester polyol.

The similar processes mentioned above include use by Alder and Stein of palladium as a catalyst to polymerize and hydrogenate DCP into the trimer form, then to tetracyclopentadiene, and finally into pentacyclopentadiene. Hydrogenation and polymerization to tetrahydrotricyclopentadiene has also been accomplished with Adams' platinum catalyst at room temperature and fifty pounds per square inch pressure. Bai, Zhang, and Sachtler of the Center for Catalysis and Surface Science, Northwestern University, reported using palladium adducts in 1991 for cyclization and hydrogenolysis reactions of neopentane and other hydrocarbons. U.S. Pat. No. 4,178,455 to Hirai et al. teaches that a transition metal catalyst, with a Lewis acid promoter, will convert urea, biurets, and allophanates into corresponding urethanes.

It is an object of the present invention to provide a thermosetting foam utilizing the advantages of specially synthesized cyclopentane ("SYNCP") as an improved insulating gas inside closed cells.

Another advantage of the present invention is the utilization of a hydrocarbon blowing agent which is readily miscible with common polyester polyols without requiring organic surfactants to make a stable blend.

An advantage of the present invention is the ability to create a foamable blend viscosity low enough to use in existing pumps without the requirement for additional viscosity reducing diluents.

Yet another advantage of the present invention is the utilization of an abundant source of specially synthetically produced cyclopentane, which insures that the costs will be contained in a reasonable range.

Still another advantage of the present invention is the achievement of a thermosetting foam having an ASTM E-84 Flame Spread Index less than the maximum 75 allowed.

SUMMARY

A thermosetting plastic foam solid is obtained using a blowing agent comprised at least partially of the reaction product of the cracking of dicyclopentadiene into essentially pure cyclopentane. This unique cyclopentane hydrocarbon is miscible in polyester polyols, where others, such as extracted cyclopentane, are not. In a blend of 15 parts of liquid flame retardant per hundred parts polyester polyol, the mixture is both stable and has a suitably low viscosity.

DETAILED DESCRIPTION OF THE INVENTION

It has been surprising to discover that cyclopentane synthesized from dicyclopentadiene ("DCP"), $C_{10}H_{12}$, is miscible with polyester polyols, not requiring additional surfactants or emulsifiers to mix well. As one skilled in the art will now appreciate upon comprehending this discovery, the miscibility of this unique cyclopentane creates a foamable blend having a viscosity low enough to utilize, whereas the EXTRCP does not create this advantage.

The unique, or special, synthesized cyclopentane (SYNCP) utilized in all embodiments of this invention is obtained from Exxon Chemical Americas as imported "Exxsol Cyclopentane". In this regard, the cyclopentane utilized in all embodiments of this invention is synthetically created by the depolymerization of DCP to CP. The synthetic cyclopentane used in the examples of this invention is in excess of 95% pure cyclopentane.

The simplified equation for synthesized cyclopentane (SYNCP) according to the present invention is as shown as EQUATION 1:

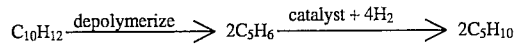

$$C_{10}H_{12} \xrightarrow{\text{depolymerize}} 2C_5H_6 \xrightarrow{\text{catalyst} + 4H_2} 2C_5H_{10}$$

Examples of processes suitable for production of the synthesized cyclopentane (SYNCP) according to the present invention are described in GB 2,271,575A and GB 2,273,107A, both of which are incorporated herein by reference. In GB 2,271,575A, cyclopentane is used as a diluent, or carrier, during the depolymerization, e.g., "cracking", stage to reduce coking and the formation of trimers, tetramers, and higher polymers which are not readily decomposed to the monomer, as taught in GB 1,302,481, also incorporated herein by reference. In GB 2,273,107A, catalyst powder is circulated through reaction zones in a slurry form until it is removed by filtration. This processing method allows the hydrogenation of the unsaturated monomer to cyclopentane at temperatures below 175° C. The advantages of this process are outlined in GB 1,115,145 and GB 1,264,255, both of which are incorporated herein by reference.

As another example of an implementation of EQUATION 1, the $C_5H_6$ represents the unsaturated five-carbon hydrocarbons, either linear or cyclic. Some pentadiene ($C_5H_8$) may also be present during the conversion. In such process, the cyclopentadiene is hydrogenated to cyclopentane, and the pentadiene may undergo hydrogenation and cyclization to cyclopentane using a catalyst, e.g., a transition metal (or adducts thereof) catalyst. An example of a palladium metal adduct is $PdCl_2$.

The miscibility of the specially synthesized cyclopentane (SYNCP) of the invention is evidenced by TABLE III.

Furthermore, the addition of a potassium catalyst, a tertiary amine catalyst, and the normal silicone type surfactant to the above blends of synthesized cyclopentane (SYNCP) produces clear solutions in the useful ranges of from about 13% up to about 30% cyclopentane by weight. By contrast, these same additives do not make clear solutions of any ratio blend with the three blowing agents of TABLE I.

TABLE III

| MISCIBILITY STUDIES OF THE PRESENT CYCLOPENTANE INVENTION | |
|---|---|
| Weight Ratio of Polyol/Cyclopentane | Synthesized Cyclopentane |
| 80/20 | Stable Mixture |
| 75/25 | Stable Mixture |
| 70/20 | Stable Mixture |
| 50/50 | Stable Mixture |
| 35/65 | Stable Mixture |
| 20/80 | Stable Mixture |

In contrast to the high viscosities shown in TABLE II utilizing extracted cyclopentane, as shown in TABLE IV foamable mixtures using the specially synthesized cyclopentane (SYNCP) of the invention have low viscosities. Furthermore, the mixtures of the invention were all clear solutions and remained stable.

It is well known that organic surfactants contribute to plastic foam flammability, whereas propylene carbonate does not. Thus, the foam of Example 8 in TABLE IV utilizing 10 pphp propylene carbonate has a lower Flame Spread Index than the foam of Example 10 utilizing 10 pphp ethoxylated nonylphenol (Texaco NP-95). Advantageously, Example 8 also has a lower viscosity than Example 10, although both are low enough to use easily. Thus, the use of an organic carbonate in place of an organic surfactant is a major advantage not available to the extracted cyclopentane (EXTRCP), as evidenced by the broken emulsions in TABLE II.

Thus it can be seen by comparing TABLE II with TABLE IV, that the synthesized cyclopentane affords lower, workable viscosities even at the low temperature of 65° F.

Table V shows blends with, and without, liquid flame retardants (Fyrol PCF), with either extracted cyclopentane (EXTRCP) or synthetic cyclopentane (SYNCP), as well as their Brookfield viscosities at 77° F.

retardant added are low enough (below 1700 cps) to be easily used in any foam machinery. Conversely, without a liquid flame retardant being utilized, the viscosities are over 3000 cps.

Vapor thermal conductivity properties of four blowing agents are shown below in TABLE VI, including one blowing agent from the past (CFC-11), one blowing agent from the present (HCFC-141b), a purported blowing agent of the future (n-pentane), and the SYNCP blowing agent of the present invention.

TABLE VI

| | VAPOR THERMAL CONDUCTIVITY: | |
|---|---|---|
| BLOWING AGENT | mW/m° K. at 25° C. | BTU in/hr * ft$^2$ * °F. at 140° F. |
| CFC-11 | 7.80 | 0.0648 |
| HCFC-141b | 9.80 | 0.0960 |
| n-Pentane | 14.80 | 0.1080 |
| SYNCP | 12.10 | 0.0864 |

TABLE IV

| | FOAMABLE BLEND EXAMPLES 1–10 | | | | | | | | | |
|---|---|---|---|---|---|---|---|---|---|---|
| CHEMICALS: | Ex 1 Pbw | Ex 2 Pbw | Ex 3 Pbw | Ex 4 Pbw | Ex 5 Pbw | Ex 6 Pbw | Ex 7 Pbw | Ex 8 Pbw | Ex 9 Pbw | Ex 10 Pbw |
| PS-A | 100 | 100 | 100 | 100 | 100 | 100 | 100 | 100 | 100 | 100 |
| Fyrol PCF | — | — | — | — | — | 15 | 15 | 15 | 15 | 15 |
| Dabco K-15 | 4.0 | 4.0 | 4.0 | 4.0 | 4.0 | 4.0 | 4.0 | 4.0 | 4.0 | 4.0 |
| PM-DETA | 0.2 | 0.2 | 0.2 | 0.2 | 0.2 | 0.2 | 0.2 | 0.2 | 0.2 | 0.2 |
| DC-5357 | 2.0 | 2.0 | 2.0 | 2.0 | 2.0 | 2.0 | 2.0 | 2.0 | 2.0 | 2.0 |
| Water | — | — | — | — | — | 1.8 | 1.8 | 1.8 | 1.8 | 1.8 |
| Prop Carb | — | 5.0 | 10 | — | — | — | 5.0 | 10 | — | — |
| Tex NP-95 | — | — | — | 5.0 | 10 | — | — | — | 5.0 | 10 |
| SYNCP | 20. | 20. | 20. | 20. | 20. | 23. | 23. | 23. | 23. | 23. |
| Brookfield Viscosity cps at 65° F. = | 3416 | 2680 | 1248 | 3104 | 2200 | 2148 | 1344 | 874 | 1432 | 942 |

TABLE V

| | FOAMABLE BLEND EXAMPLES 11–22 | | | | | | | | | | | |
|---|---|---|---|---|---|---|---|---|---|---|---|---|
| CHEMICALS: | Ex 11 Pbw | Ex 12 Pbw | Ex 13 Pbw | Ex 14 Pbw | Ex 15 Pbw | Ex 16 Pbw | Ex 17 Pbw | Ex 18 Pbw | Ex 19 Pbw | Ex 20 Pbw | Ex 21 Pbw | Ex 22 Pbw |
| PS-2502A | 100 | 100 | 100 | 100 | 100 | 100 | 100 | 100 | 100 | 100 | 100 | 100 |
| Fyrol PCF | — | — | — | — | — | — | 15 | 15 | 15 | 15 | 15 | 15 |
| Dabco K-15 | 4.0 | 4.0 | 4.0 | 4.0 | 4.0 | 4.0 | 4.0 | 4.0 | 4.0 | 4.0 | 4.0 | 4.0 |
| PM-DETA | 0.2 | 0.2 | 0.2 | 0.2 | 0.2 | 0.2 | 0.2 | 0.2 | 0.2 | 0.2 | 0.2 | 0.2 |
| Silicone | 2.6 | 2.6 | 2.6 | 2.6 | 2.6 | 2.6 | 2.6 | 2.6 | 2.6 | 2.6 | 2.6 | 2.6 |
| EXTRCP | 21.7 | — | 25.3 | — | 29.1 | — | 21.7 | — | 25.3 | — | 29.1 | — |
| SYNCP | — | 21.7 | — | 25.3 | — | 29.1 | — | 21.7 | — | 25.3 | — | 29.1 |
| Brookfield Viscosity cps at 77° F. = | 5320 | 3168 | 6072 | 3120 | 7192 | 3160 | 2120 | 1408 | 2336 | 1440 | 3552 | 1680 |

One skilled in the art will notice a unique situation: with both versions of cyclopentane, as the amount of cyclopentane increases, so does the viscosity. This is in contrast to prior art blowing agents, which decrease viscosity with increased amount of blowing agent. Nevertheless, it is evident from TABLE V data that synthesized cyclopentane (SYNCP) not only produces lower viscosities than extracted cyclopentane (EXTRCP), the viscosities produced with about 15 parts by weight (per hundred polyol) liquid flame It should be noted that at higher temperatures (140° F.), the SYNCP exhibits a better intrinsic insulation value than the currently utilized HCFC-141b. In general, TABLE VI shows the advantage of SYNCP over n-pentane as a potential future insulating gas.

TABLE VII shows thermosetting foam examples and illustrates the surprising differences between extracted (EXTRCP) and synthesized cyclopentane (SYNCP) of the present invention. Thus, TABLE VII demonstrates that when the extracted cyclopentane (EXTRCP) is compared directly to synthesized cyclopentane (SYNCP), the synthesized cyclopentane of the present invention shows unexpected and favorable results. All examples of the synthesized cyclopentane show better k-factors, and lower densities. All of the friabilities were lower than foam blown with prior art blowing agents. At the higher 3.0 Index, and the highest water level (0.85 parts per hundred parts polyol), the synthesized cyclopentane produced a foam with 24.5% lower friability than the extracted cyclopentane counterpart.

SYNCP has a better intrinsic insulating value than three of the four HFCs listed.

In view of the foregoing, preferably the foamable blend which contains most of the synthesized cyclopentane also utilizes a liquid fire retardant. The most preferred embodiments of the instant invention also utilize (1) a lower boiling point alkane blowing agent with the specially synthesized cyclopentane (SYNCP) to increase internal cell gas pressure as a protection against shrinkage and [optionally] (2) a polar organic blowing (e.g, expansion) agent which azeotropes

TABLE VII

THERMOSETTING FOAM EXAMPLES 1–8

| COMPONENT (pbw) | Ex. 1 | Ex. 2 | Ex. 3 | Ex. 4 | Ex. 5 | Ex. 6 | Ex. 7 | Ex. 8 |
|---|---|---|---|---|---|---|---|---|
| PS-2502A | 100.0 | 100.0 | 100.0 | 100.0 | 100.0 | 100.0 | 100.0 | 100.0 |
| Potassium Cat. | 2.7 | 2.7 | 3.0 | 3.0 | 3.2 | 3.2 | 4.0 | 4.0 |
| Tertiary Amine | 0.2 | 0.2 | 0.2 | 0.2 | 0.15 | 0.15 | 0.15 | 0.15 |
| Silicone | 2.2 | 2.2 | 2.1 | 2.1 | 2.1 | 2.1 | 2.0 | 2.0 |
| Water | — | — | — | — | 0.68 | 0.68 | 0.85 | 0.85 |
| EXTRCP | — | 24.0 | — | 26.9 | — | 23.4 | — | 26.7 |
| SYNCP | 24.0 | — | 26.9 | — | 23.4 | — | 26.7 | — |
| TOTAL B-SIDE | 129.1 | 129.1 | 132.2 | 132.2 | 129.53 | 129.53 | 133.7 | 133.7 |
| Lupr. M70L | 146.7 | 146.7 | 176.7 | 176.7 | 170.3 | 170.3 | 208.9 | 208.9 |
| Silicone | 0.4 | 0.4 | 0.5 | 0.5 | 0.4 | 0.4 | 0.5 | 0.5 |
| TOTAL A-SIDE | 147.1 | 147.1 | 177.2 | 177.2 | 170.7 | 170.7 | 209.4 | 209.4 |
| TOTAL FOAM | 276.2 | 276.2 | 309.4 | 309.4 | 300.23 | 300.23 | 343.1 | 343.1 |
| INDEX, NCO/OH | 2.5 | 2.5 | 3.0 | 3.0 | 2.5 | 2.5 | 3.0 | 3.0 |
| DENSITY, PCF | 1.6 | 1.7 | 1.6 | 1.7 | 1.5 | 1.6 | 1.6 | 1.7 |
| CREAM TIME | 18" | 19" | 19" | 20" | 22" | 23" | 21" | 22" |
| GEL TIME | 30" | 30" | 28" | 29" | 39" | 42" | 42" | 43" |
| STRING TIME | 44" | 44" | 43" | 43" | 48" | 49" | 51" | 52" |
| TACK FREE | 47" | 46" | 45" | 46" | 52" | 53" | 53" | 55" |
| FRIABILITY, % Weight Loss | 2.57 | 2.39 | 2.94 | 2.61 | 3.60 | 2.96 | 7.88 | 10.43 |
| INITIAL k | 0.1401 | 0.1539 | 0.1397 | 0.1528 | 0.1377 | 0.1515 | 0.1397 | .1508 |
| Percent Better R-Value with SYNCP | 9.9% | | 9.4% | | 10.0% | | 8.0% | |

To further put the potential future insulating gases in perspective, several proposed HFC gases are added in TABLE VIII to the pentane isomers and the prior art fluorocarbons, showing respective insulation data.

TABLE VIII

VAPOR THERMAL CONDUCTIVITY:

| BLOWING | BTU in/hr * ft$^2$ * °F. | | mW/m° K. | |
|---|---|---|---|---|
| AGENT | [1]at 140° F. | [2]at 44° C. | [3]at 20° C. | [4]at 25° |
| CFC-11 | 0.0648 | 0.064 | 8.4 | 7.8 |
| HCFC-141b | 0.0960 | 0.084 | 9.7 | 9.8 |
| HFC-245ca | — | 0.092 | 13.3 | — |
| HFC-245fa | — | 0.097 | — | — |
| HFC-356mffm | — | 0.102 | — | — |
| HFC-365mfc | — | — | 10.6 | — |
| SYNCP | 0.0864 | — | 12.0 | 12.1 |
| n-pentane | 0.1080 | — | — | 14.8 |

[1]Dow Chemical Company.
[2]Knopeck, Parker, Richard, Shankland, "Polyurethanes 1994, Page 116.
[3]Murphy, J., & Costa, J., 'Polyurethanes 1994', Proceedings, Page 323.
[4]BASF Chemical Company.
(Different data sources show slightly different conductivity values.)

By noting the lambda values in the third column of TABLE VIII, one can compare cyclopentane (SYNCP) to HFC-245ca and HFC-365mfc. Then, by using HFC-245ca to interpolate that data into the second column, one can see that with cyclopentane such as taught in U.S. Pat. No. 5,166,182, or a viscosity depressant such as propylene carbonate or the non-ionic surfactants such as ethoxylated nonylphenol. The latter are especially useful if the foamable blend is to be cooled below 70° F. prior to use.

Suitable flame retardants utilized in the invention include, but are not limited to, tri(2-chloroisopropyl) phosphate, tricresyl phosphate, tri (2 -chloroethyl) phosphate, tri (2,2-dichloroisopropyl)phosphate, diethyl N,N-bis (2hydroxyethyl) aminomethylphosphonate, dimethyl methylphosphonate, tri (2,3 -dibromopropyl)phosphate, tri (1,3-dichloropropyl)phosphate, and tetra-kis-(2-chloroethyl)ethylene diphosphate.

The isocyanates utilized may be any organic isocyanate. However, the most preferred type is the polymeric polymethylene polyphenylisocyanate having an average functionality of between 2.0 and 3.5.

The polyester polyols preferred for this invention are those aromatic organic esters based upon one, or a combination, of the phthalate isomers linked together with mixed glycols, predominately diethylene glycol.

Any of the prior art catalysts and cell stabilizing surfactants may be utilized. However, the potassium-organo-salt catalysts are preferred.

Thermosetting Foam Examples 9 through 15 in TABLE IX show the most preferred foam formulations.

In thermosetting Foam Examples 9 through 15, any HCFC or HFC may be substituted for, or mixed with, any of the additional expansion agents; e.g., propane, iso-butane, acetone, methyl/ethyl alcohol, or methyl acetate. One skilled in the art will recognize that other combinations of the components shown in TABLE IX can be interchanged, or intermixed, or added at different levels, to provide a thermoserring foam with different properties.

Advantageously, the abundance of DCP makes it an ideal raw material for the synthesis of pure cyclopentane according to the present invention.

As an additional advantage, as understood with reference to the foregoing examples, the use of SYNCP faciliates the use of little or no organic surfactants for either compatability or viscosity reduction, so that the foamable blends of the present invention are substantially devoid of organic surfactants.

Thermosetting Foam Examples 16 and 17 (see TABLE X) show the use of polyether polyols in conjunction with polyester polyols. These foams are suitable for non-construction foams used in the United States, such as appliance insulation, and for a wide range of foreign (e.g., European) rigid foam applications, including building construction. Ranging from an Index of 1.5 up to 3.0, the foams of Examples 16 and 17 provide good insulating properties with differing flammability resistance.

When selecting various flame retardants, the advantages of synthetic cyclopentane (SYNCP) was again demonstrated. As in TABLE IV and TABLE V above, TABLE XII below shows the Brookfield viscosities of blend examples 23A–23F of TABLE XI. Blend examples 23A–23F differ only in the particular flame retardant utilized (the same amount of flame retardant being utilized in each example). As seen in TABLE XI, the only flame retardant soluble in both types of pentane (e.g., both SYNCP and EXTRCP) is Fyrol PBR.

TABLE XI

FOAMABLE BLEND EXAMPLES 23A–23F

| Chemicals | Pbw |
| --- | --- |
| Stepan PS-2502A | 100.0 |
| Flame Retardant | 15.0 |
| Propylene Carbonate | 5.0 |
| Texaco NP-95 | 5.0 |
| Dabco K-15 | 3.2 |
| Tertiary Amine | 0.1 |
| Silicone Surfactant | 2.6 |
| Pentane | 23.5 |

TABLE XII

BROOKFIELD VISCOSITY AT 65° F.

| Example | Flame Retardant | SYNCP | EXTRCP |
| --- | --- | --- | --- |
| 23A | Fyrol PCF | 1184 | 1784* |
| 23B | Fyrol DMMP | 644 | 1040* |
| 23C | Fyrol CEF | 1564 | 2712* |
| 23D | Fyrol-6 | 1520 | 2296* |
| 23E | Fyrol-PBR | 1680 | 1940 |
| 23F | Fyrol-2 | 1540 | 2092* |

In TABLE XII, an asterisk (*) indicates an unstable (e.g., separated) mixture.

The amount of liquid flame retardant should be in the range of 5–30 pphp (parts per hundred polyol), and preferably is in the range of 10–20 pphp.

The preferred levels of propylene carbonate utilized are in the range of 5.00 pphp to 15.0 pphp, with the most preferred embodiment being 7.5 to 10.0 pphp. The preferred range of organic non-ionic surfactant utilized is between 0.0 and 10.0 pphp, with the most preferred embodiment being from 5.0 to 10.00 pphp. It was discovered that an equal weight ratio of propylene carbonate to non-ionic organic surfactant was the optimum balance of these different types of diluent.

As understood by those skilled in the art, the term "Index" as employed herein refers to the ratio of isocyanate functional groups to polyol functional groups.

While the invention has been particularly shown and described with reference to the preferred embodiments thereof, it will be understood by those skilled in the art that various alterations in form and detail may be made therein without departing from the spirit and scope of the invention.

TABLE IX

THERMOSETTING FOAM EXAMPLES 9–15

| COMPONENT, pbw | Ex. 9 | Ex. 10 | Ex. 11 | Ex. 12 | Ex. 13 | Ex. 14 | Ex. 15 |
| --- | --- | --- | --- | --- | --- | --- | --- |
| PS-2502A | 100.0 | 100.0 | 100.0 | 100.0 | 100.0 | 100.0 | 100.0 |
| Fyrol PCF | 15.0 | 15.0 | 15.0 | 15.0 | 15.0 | 15.0 | 15.0 |
| Dabco K-15 | 4.0 | 4.0 | 4.0 | 4.0 | 4.0 | 4.0 | 4.0 |
| Amine Cat. | 0.3 | 0.3 | 0.3 | 0.3 | 0.3 | 0.3 | 0.3 |
| Silicone | 2.5 | 2.5 | 2.5 | 2.5 | 2.5 | 2.5 | 2.5 |
| Prop. Carb. | 5.0 | 10.0 | 10.0 | 10.0 | 10.0 | 10.0 | 10.0 |
| Texaco NP95 | 5.0 | 0.0 | 0.0 | 0.0 | 0.0 | 0.0 | 0.0 |
| Acetone** | 0.0 | 0.0 | 0.0 | 10.44 | 0.0 | 0.0 | 0.0 |
| Methyl Acetate** | 0.0 | 0.0 | 0.0 | 0.0 | 0.0 | 10.99 | 0.0 |
| Methyl Alcohol** | 0.0 | 0.0 | 0.0 | 0.0 | 0.0 | 0.0 | 4.06 |
| Propane*** | 0.0 | 1.0 | 0.0 | 0.0 | 0.0 | 0.0 | 0.0 |

TABLE IX-continued

THERMOSETTING FOAM EXAMPLES 9-15

| COMPONENT, pbw | Ex. 9 | Ex. 10 | Ex. 11 | Ex. 12 | Ex. 13 | Ex. 14 | Ex. 15 |
|---|---|---|---|---|---|---|---|
| Iso-Butane*** | 0.0 | 0.0 | 4.1 | 0.0 | 0.0 | 0.0 | 0.0 |
| Water | 1.5 | 0.0 | 0.0 | 0.0 | 0.0 | 0.0 | 0.0 |
| SYNCP | 20.0 | 28.7 | 25.6 | 18.56 | 26.82 | 18.01 | 24.94 |
| TOTAL B-SIDE | 153.3 | 161.5 | 161.5 | 160.8 | 160.8 | 160.8 | 160.8 |
| Lupr. M70L | 230.0 | 178.8 | 178.8 | 178.8 | 178.8 | 178.8 | 178.8 |
| Silicone | 0.5 | 0.5 | 0.5 | 0.5 | 0.5 | 0.5 | 0.5 |
| TOTAL A-SIDE | 230.5 | 179.3 | 179.3 | 179.3 | 179.3 | 179.3 | 179.3 |
| TOTAL FOAM | 383.8 | 340.8 | 340.8 | 340.8 | 340.8 | 340.8 | 340.8 |
| Foam Index | 2.68 | 3.0 | 3.0 | 3.0 | 3.0 | 3.0 | 3.0 |
| Flame Spread Index | 36 | less than 75 | less than 75 | less than 75 | less than 75 | less than 75 | less than 75 |

**"These polar organic expansion agents are mixed at the weight percent ratio with the special synthesized cyclopentane which forms an azeotrope boiling at a lower temperature than either component alone.
***These alkanes are mixed with special synthesized cyclopentane in a weight ratio which produces the same vapor-pressure-verses-temperature curve as CFC-11.

TABLE X

THERMOSETTING FOAM EXAMPLES 16-17

| COMPONENT, pbw | Ex. 16 | Ex.17 |
|---|---|---|
| Stepan 2352 | 51.00 | 51.0 |
| Voranol 280 | 49.00 | 49.0 |
| Fyrol PCF | 15.0 | 15.0 |
| Dabco K-15 | 4.5 | 2.0 |
| Prop. Carb. | 5.0 | 5.0 |
| Texaco NP95 | 5.0 | 5.0 |
| OSI-51000 | 2.47 | 2.47 |
| PM-DETA | 0.25 | 0.15 |
| Water | 0.379 | 0.379 |
| SYNCP | 21.72 | 21.72 |
| TOTAL B-SIDE | 154.3 | 151.72 |
| PMDI | 213.10 | 104.0 |
| DC-5098 | 0.53 | 0.53 |
| SYNCP | 10.66 | 5.2 |
| TOTAL A-SIDE | 224.29 | 109.73 |
| TOTAL FOAM | 378.60 | 261.45 |
| Foam Index | 3.0 | 1.5 |
| Flame Spread Index | >75 | >450 |

For the present invention, a majority (e.g., greater than 50% parts by weight) of the polyol component should be polyester polyol, although as shown in TABLE X a minority of the polyol component may be a polyether polyol (e.g., Voranol 280).

The embodiments of the invention in which an exclusive property or privilege is claimed are defined as follows:

1. A method of producing a rigid thermosetting plastic foam, the method comprising the steps of:
   (1) preparing a first of two foam forming blends using polymeric polymethylene polyphenylisocyanate;
   (2) preparing a second of two foam forming blends by mixing together:
   a polyol component comprised of a majority of polyester polyol;
   a liquid flame retardant;
   a suitable catalyst to promote the reaction between the first of two foam forming blends and the polyol component; and,
   a blowing agent comprised at least partially from depolymerization of dicyclopentadiene to yield cyclopentane; and,
   (3) mixing together the first and second foam forming blends to form the rigid thermosetting plastic foam.

2. The method of claim 1, wherein the cyclopentane obtained from step (2) permits both the first and second foam forming blends to be substantially devoid of an organic surfactant.

3. The method of claim 1, wherein the foam has a ratio of isocyanate functional groups to polyol functional groups greater than 1.5:1.0.

4. The method of claim 1, wherein the blowing agent comprised at least partially of the reaction product of the reactions:
   i) the depolymerization of dicyclopentadiene into unsaturated five-carbon hydrocarbons; plus,
   ii) the catalytic hydrogenation of the unsaturated five-carbon hydrocarbons into cyclopentane.

5. The method of claim 1, wherein other foam expansion agents are utilized with said blowing agent.

6. The method of claim 5, wherein the other foam expansion agents are alkanes having four or less carbon atoms.

7. The method of claim 5, wherein the other foam expansion agents are polar organic solvents forming azeotropes with cyclopentane.

8. The method of claim 5, wherein the other foam expansion agents are partially hydrogenated chlorofluorocarbons.

9. The method of claim 5, wherein the other foam expansion agents are partially hydrogenated fluorocarbons.

10. The method of claim 1, wherein the liquid flame retardant is chosen from a group consisting of tri (2-chloroisopropyl)phosphate, tricresyl phosphate, tri (2-chloroethyl)phosphate, tri (2,2-dichloroisopropyl)phosphate, diethyl N,N-bis (2-hydroxyethyl) aminomethylphosphonate, dimethyl methylphosphonate, tri (2,3-dibromopropyl)phosphate, tri(1,3-dichloropropyl)phosphate, and tetra-kis-(2-chloroethyl)ethylene diphosphate.

11. The method of claim 1, wherein the said reaction product is at least 95% pure cyclopentane.

12. The method of claim 1, wherein the polyol component is a polyester polyol having a hydroxyl number between 190 and 340.

13. The method of claim 1, wherein the polyol component is comprised of greater than 50% by weight polyester and less than 50% by weight polyether polyol.

14. The method of claim 1, wherein the second of the two foaming blends is a clear, stable mixture having a Brookfield viscosity below 1700 cps at 77° F.

15. The method of claim 1, wherein one of the forming blends includes an organic carbonate.

* * * * *

UNITED STATES PATENT AND TRADEMARK OFFICE
Certificate

Patent No. 5,578,652  Patented: November 26, 1996

On petition requesting issuance of a certificate for correction of inventorship pursuant to 35 U. S. C. 256, it has been found that the above-identified patent, through error and without deceptive intent, improperly sets forth the inventorship.

Accordingly, it is hereby certified that the correct inventorship of this patent is: Robert H. Blanpied, Meridian, Miss.; James D. Thornsberry, Meridian, Miss. and Steven E. Silverberg, Seabrook, Tex.

Signed and Sealed this Twenty-Third Day of December, 1997.

JIM SEIDLECK, *SPE*
Art Unit 1207